United States Patent
Cohen et al.

(10) Patent No.: US 7,483,924 B2
(45) Date of Patent: Jan. 27, 2009

(54) METHODOLOGY FOR MAPPING HL7 V2 STANDARDS TO HL7 V3 STANDARDS

(75) Inventors: Simona Cohen, Haifa (IL); Roni Ram, Yokne'am Ilit (IL)

(73) Assignee: International Business Machines Corporation, Armonk, NY (US)

( * ) Notice: Subject to any disclaimer, the term of this patent is extended or adjusted under 35 U.S.C. 154(b) by 437 days.

(21) Appl. No.: 11/037,593

(22) Filed: Jan. 18, 2005

(65) Prior Publication Data

US 2006/0161840 A1   Jul. 20, 2006

(51) Int. Cl.
*G06F 17/30* (2006.01)
*G06F 7/02* (2006.01)
*G06F 7/14* (2006.01)

(52) U.S. Cl. ............. 707/203; 707/104.1; 707/201
(58) Field of Classification Search ......... 715/513; 707/104.1, 203
See application file for complete search history.

(56) References Cited

U.S. PATENT DOCUMENTS

| 2003/0088438 A1* | 5/2003 | Maughan et al. ............. 705/2 |
| 2003/0088543 A1* | 5/2003 | Skeen et al. ............. 707/1 |
| 2005/0005233 A1* | 1/2005 | Kays et al. ............. 715/500.1 |
| 2005/0273367 A1* | 12/2005 | Nourie et al. ............. 705/3 |

OTHER PUBLICATIONS

Dolin RH, Rishel W, Biron PV, Spinosa J, Mattison JE, "SGML and XML as interchange formats for HL7 messages", Proc AMIA Symposium, 1998, pp. 720-724.*

* cited by examiner

*Primary Examiner*—Kuen S Lu
*Assistant Examiner*—Patrick Sweeney

(57) ABSTRACT

A method for converting communications messages includes accepting a set of related HL7 V2 messages to be converted, the messages conforming to HL7 V2 specifications. Additionally, an XML schema derived from an HL7 V3 specification Reference Information Model (RIM) is given, and conversion mapping rules are provided. The V2 messages are automatically converted to a V3 message or document, conforming to the selected XML schema, using the conversion mapping rules.

9 Claims, 2 Drawing Sheets

METHODOLOGY FOR MAPPING HL7 V2 STANDARDS TO HL7 V3 STANDARDS

FIELD OF THE INVENTION

The present invention relates generally to healthcare computer systems, and specifically to methods and systems for constructing and exchanging healthcare-related information in computer systems.

BACKGROUND OF THE INVENTION

Health Level Seven (HL7) is a standards-producing body, which develops data standards for storing and exchanging information across the healthcare industry. HL7's mission statement is "To provide a comprehensive framework and related standards for the exchange, integration, sharing, and retrieval of electronic health information that supports clinical practice and the management, delivery and evaluation of health services. Specifically, to create flexible, cost effective standards, guidelines, and methodologies to enable healthcare information system interoperability and sharing of electronic health records."

The HL7 standards cover both clinical and administrative aspects of the healthcare industry, including laboratory, clinical genomics, medical records, patient care, pharmacy, public health reporting, regulated studies, accounts and billing, claims and reimbursement, patient administration and personnel management scheduling.

From 1990 until 2003, HL7 produced a family of message specifications denoted HL7 Version 2. The latest specification in the family is HL7 V2.5, which is incorporated herein by reference. Further information regarding HL7 standards is available at www.hl7.org/library/standards_non1.htm.

HL7 V2 messages contain information regarding healthcare-related events such as doctor visits, laboratory test results, and patient observations. The following is a sample V2 message reporting laboratory test results:

```
MSH|^~\&|||||19941122100053||ORU^M01|
EVN|M01|199411181141|
PID|||661041||GARDNER^REED^M|
PV1||I|E7^703^^LDS|
OBR||^A000520|LYTES^Serum Electrolytes|
OBX|1|NM|NAS^Serum Sodium|1|138|mmol/L|
OBX|2|NM|K^Serum Potassium|1|3.2|mmol/L|
OBX|3|NM|CL^Serum Chloride|1|114|mmol/L|
OBX|4|NM|CO2^Serum CO2|1|24|mmol/L|
```

Each V2 message consists of segments, represented by rows in the example shown above. Each segment begins with a three-letter code defining the segment type. The first segment is the message header, denoted MSH. The PID ("patient Identifier") segment contains patient identification information. Other segment types include PV1, which stands for "patient visit," and OBX, which stands for "observation." A table listing additional segment types is given in the detailed description section hereinbelow.

HL7 V2 segments are divided into data fields, separated by vertical bar symbols, each field containing data elements. Data elements may conform to any of several data types including text characters, such as a patient name, or numerical information, such as a patient age or a quantitative blood test result. Complex data types, including two or more data elements, are also defined. Data fields may be defined as "required" or "optional," and may be repeated several times within a segment.

During the late 1990's, work began on a new family of message specifications, later to be published as the HL7 V3 specification. HL7 V3 follows an XML structure. For a better understanding of the methods to be described, the concept of XML-based structures will now be explained in greater detail.

XML (Extensible Markup Language) is a simplified version of Standard Generalized Mark-Up Language (SGML), designed initially for Web documents. XML allows designers to create their own customized markup languages, enabling the definition, transmission, validation, and interpretation of data between applications and between organizations. XML is a formal recommendation of the World Wide Web Consortium (W3C). Additional information regarding XML is available at www.w3c.org/xml. Markup symbols are used in XML to describe the contents of a page or file, defining the meaning of the data that is being described. The term "markup" refers to a sequence of characters or other symbols that are inserted at certain places in a document, to describe the document's storage layout and logical structure. The markup symbols are often called "tags." XML is extensible due to the fact that the markup tags are user-defined, thereby enabling the designer to define a complete language to suit a particular application. The designer defines a DTD, or Document Type Definition, which is a collection of XML markup declarations that, as a collection, defines the structure, elements, and attributes that are available for use in a document that complies with the DTD. The designer may also use the newer XSD, or XML Schema Definition format for defining tags.

The HL7 V3 family of specifications is centered around a single, unified Reference Information Model (RIM) covering all domains of the healthcare industry. The RIM defines all data structures, data types and vocabularies, as well as the relationships between them. The RIM includes dozens of classes, representing the building blocks from which all healthcare-related messages and documents are built.

Four fundamental classes are defined: Entity, Role, Participation and Act. Other classes are typically specializations of one of the fundamental classes. For example, a Procedure class representing a medical procedure is a specialization of the Act class. Observations are specializations of Acts as well, representing laboratory orders and results, diagnoses and more. Patients and healthcare providers are represented through the associations of Entity-Role-Participation.

For example, a person is an Entity that may have the Role of a physician and the Participation of an attending physician in the Act of admitting a patient to a hospital. Each class contains attributes that carry information about the class. Each attribute is formatted according to a predefined data type. The class attributes and data types are defined in the RIM. Using this class representation, any healthcare-related event can be expressed in terms of a unified, predefined data structure. Further details regarding HL7 V3 can be found at www.hl7.org/library/standards_non1.htm.

All HL7 V3 specifications are reductions or specializations of the RIM to address the needs of specific usages in the healthcare industry. For example, the Clinical Document Architecture (CDA) is a specification for producing and exchanging clinical documents, derived from the HL7 RIM, in a standard, XML-based structure. Further details of the CDA specifications can be found in a publication by Dolin, et al. entitled "HL7 Clinical Document Architecture, Release 2, Committee Ballot #02," Dec. 8, 2003, published by the HL7 Structured Documents Technical Committee, which is incorporated herein by reference. The CDA specification documentation is also available from www.hl7.org/Library/Committees/structure/CDA.ReleaseTwo.CommitteeBallot02.Dec.2003.zip.

A derivation of the RIM for a particular usage is sometimes referred to as a "schema" or "XML schema." Other XML schemata derived from the RIM cover Regulated Clinical Research Information Management (RCRIM), Clinical-Genomics, Medication, etc.

In addition to HL7 V2 and V3, a version denoted HL7 V2.XML was approved by the HL7 organization, consisting of encoding rules for converting HL7 V2 messages into XML format. Further details regarding HL7 V2.XML are available in an HL7 Specification entitled "HL7 Version 2: XML Encoding Syntax, Release 1," Jun. 4, 2003, which is incorporated herein by reference. Several commercial conversion tools have been developed for converting HL7 V2 messages to HL7 V2.XML format. Such tools are available, for example, from iNTERFACEWARE Inc. of Toronto, Canada (www.interfaceware.com), or from Lumrix.net of Bern, Switzerland (www.1umrix.net/hl7xml.php).

SUMMARY OF THE INVENTION

The description given above illustrates some of the advantages provided by HL7 V3, in terms of representing healthcare-related messages using a single, structured, explicitly-defined information model. This representation enables semantic interoperability across platforms and applications. In other words, any HL7 V3 compliant system, regardless of the application and the computer platform it uses, can communicate with any other such system using a single interface. All data structures, logical relationships and the logical meaning assigned to those structures are inherently understood by all compliant systems.

On the other hand, HL7 V2 systems are widely deployed and V2 applications will continue to be supported and upgraded for a number of years to come. Furthermore, a significant number of medical records and databases exist that conform to the HL7 V2 specification.

Therefore, there is a particular need for converting HL7 V2 messages to HL7 V3 format. Such conversion may offer V2 applications the same level of interoperability enjoyed by V3 applications. In addition, such conversion enables V3 applications to access existing V2 databases. It should be noted that the conversion process is not a simple change of format. The semantic structure of the V3 information model must be applied to the V2 data so that the converted messages comply not only with the XML format, but also with the applicable HL7 V3 schema. HL7 V2.XML and the automatic conversion tools described hereinabove do not provide the required functionality, as HL7 V2.XML is merely a different format for representing V2 messages, without any underlying information model.

Embodiments of the present invention provide a methodology for automatically mapping sets of HL7 V2 messages into HL7 V3 XML-based messages and documents that are compliant with an XML schema derived from the HL7 V3 RIM.

There is therefore provided, in accordance with an embodiment of the present invention, a method for converting communications messages, including:

accepting a V2 message to be converted, the message conforming to an HL7 V2 specification;

accepting an XML schema, derived from an HL7 V3 specification Reference Information Model (RIM);

providing conversion mapping rules; and automatically converting the V2 message to at least one of a V3 message and a V3 document, conforming to the selected XML schema, using the conversion mapping rules.

In a disclosed embodiment, converting the V2 message includes mapping a PID (patient identification) segment in the V2 message to an XML sub-tree in the XML schema in accordance with the conversion mapping rules.

In an aspect of the present invention, converting the V2 message includes mapping the V2 message to a class in the XML schema in accordance with the conversion mapping rules. Typically, the V2 message includes a header that defines a message type, and mapping the V2 message includes decoding the message type and defining the class in accordance with the message type.

Additionally or alternatively, mapping the V2 message includes mapping segments of the V2 message to XML sub-trees of the class, in accordance with the conversion mapping rules. Typically, the XML sub-trees include attributes, and mapping the segments includes mapping data fields in the segments of the V2 message to the attributes, in accordance with the conversion mapping rules. In a disclosed embodiment, the attributes are formatted according to a data type, and mapping the data fields to the attributes includes reformatting the data fields according to the data type. In one embodiment, mapping the data fields includes creating a nested class in the XML sub-tree and mapping the data fields to the attributes of the nested class.

In a disclosed embodiment, converting the V2 message includes converting the V2 message to an HL7 V2.XML format, and mapping the message from the HL7 V2.XML format to the V3 message or document.

In another embodiment, accepting the HL7 V2 message includes receiving a set of related HL7 V2 messages, and wherein converting the V2 message includes converting the set to the V3 message or document.

There is also provided, in accordance with an embodiment of the present invention, apparatus for automatically converting communications messages, including:

a memory, which is arranged to store conversion mapping rules; and a conversion processor, which is arranged to accept a V2 message to be converted, the message conforming to an HL7 V2 specification, to accept an XML schema derived from an HL7 V3 specification Reference Information Model (RIM), and to convert the V2 message to at least one of a V3 message and a V3 document, conforming to the selected XML schema, using the conversion mapping rules.

There is additionally provided, in accordance with an embodiment of the present invention, a computer software product for automatically converting communications messages, the product including a computer-readable medium in which program instructions are stored, which instructions, when read by a computer, cause the computer to accept a V2 message to be converted, the message conforming to an HL7 V2 specification, to accept an XML schema derived from an HL7 V3 specification Reference Information Model (RIM), to provide conversion mapping rules, and to convert the V2 message to at least one of a V3 message and a V3 document, conforming to the selected XML schema, using the conversion mapping rules.

The present invention will be more fully understood from the following detailed description of the embodiments thereof, taken together with the drawings in which:

DETAILED DESCRIPTION OF EMBODIMENTS

Figure 1:
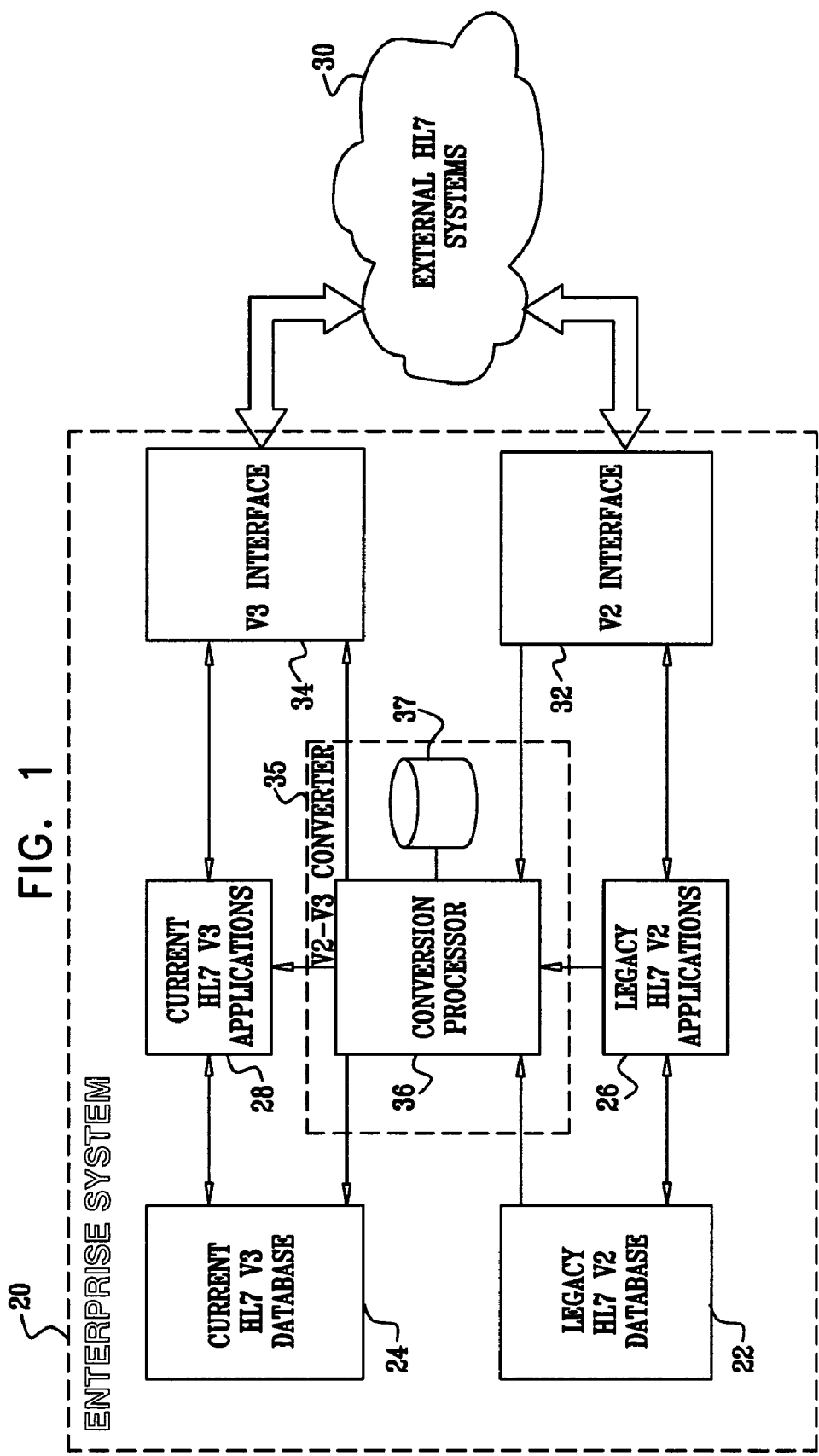
FIG. 1 is a block diagram of a healthcare computer system, in accordance with an embodiment of the present invention.

FIG. 1 is a block diagram of a healthcare enterprise computer system 20, in accordance with an embodiment of the present invention. System 20 comprises several building blocks that serve to illustrate disclosed embodiments of the present invention. Some of the building blocks may be optional in some embodiments, as will be explained hereinbelow.

System 20 is typically a mixed system comprising databases, applications and external interfaces that support either the HL7 V2 specification, or the HL7 V3 specification, or both. In this example, system 20 comprises two databases, a legacy HL7 V2 database 22 and a current HL7 V3 database 24. Similarly, system 20 comprises two sets of applications, legacy HL7 V2 applications 26 and current HL7 V3 applications 28. Applications 26 and 28 of system 20 communicate with external HL7 systems 30 using an HL7 V2 external interface 32 and a HL7 V3 external interface 34.

A V2 to V3 converter 35 is interconnected with the applications, databases and external interfaces of system 20. V2-V3 converter 35 comprises a conversion processor 36, which converts messages that conform to the HL7 V2 specification into XML-based messages and documents conforming to the HL7 V3 specification. V2-V3 converter 35 further comprises a memory containing a mapping database 37, which stores configurable mapping tables and rules, as will be explained in detail hereinbelow. Note that the term "messages," in the context of HL7, refers generally to any information stored in a database that may be conveyed in a communication message from one entity to another, as well as to the actual communication messages themselves. This broad definition of "message" is used in the present patent application and in the claims. Operations performed with respect to HL7 V3 messages in embodiments of the present invention, as described herein, may likewise be performed with respect to HL7 V3 documents unless noted otherwise.

In disclosed embodiments, V2-V3 converter 35 may perform the following functions:
   Send messages from internal V2 applications 26 to external systems 30 that conform to the V3 specification.
   Receive messages from external systems 30 that conform to the V2 specification, and transfer the messages to internal V3 applications 28.
   Send messages from internal V2 applications 26 to internal V3 applications 28.
   Enable internal V3 applications 28 to access legacy information stored in V2 database 22.
   Perform off-line upgrading of legacy V2 database 22 to V3 format by converting the V2 messages in database 22 and transferring them to V3 database 24.

V2-V3 converter 35 typically comprises a general-purpose computer, which is programmed in software to carry out the functions described herein. Alternatively, the functions of the V2-V3 converter may be distributed among multiple computers in system 20. The software may be downloaded to the computer or computers in electronic form, over a network, for example, or it may alternatively be supplied on tangible media, such as optical, magnetic or electronic storage media.

Figure 2:
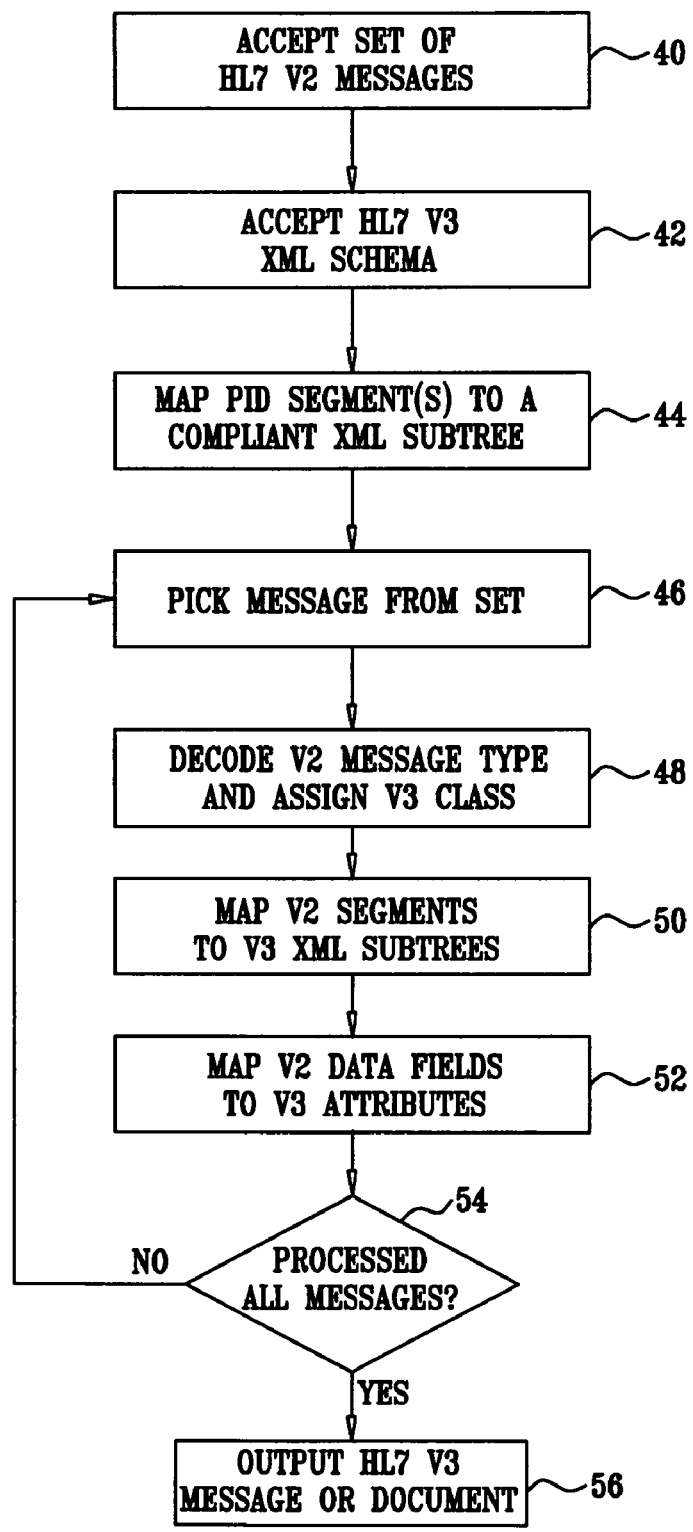
FIG. 2 is a flow chart that schematically illustrates a method for converting healthcare-related information, in accordance with an embodiment of the present invention.

FIG. 2 is a flow chart that schematically illustrates a method performed by V2-V3 converter 35 for converting healthcare-related information from HL7 V2 to HL7 V3 format, in accordance with an embodiment of the present invention. The method begins when conversion processor 36 receives a set of HL7 V2 messages at a message acceptance step 40. The method converts the set of HL7 V2 messages, typically concerning a single patient, into a single HL7 V3 message or document. The set of HL7 V2 messages may originate from any HL7 V2 application, database or external interface interconnected to the V2-V3 converter, such as the respective blocks of system 20 described in FIG. 1 hereinabove.

The HL7 V2 messages typically conform to one of two formats:
1. Vertical bar format. Each segment is represented by a row of text characters. Segments are separated by vertical bar symbols.
2. V2.XML format—An XML structure according to the V2.XML specification cited above.

The V2.XML format is functionally equivalent to the vertical bar format and is sometimes preferred as it is more readable and easier to follow. In some embodiments this structure is derived from the vertical bar representation using one of the commercial conversion tools described in the background section above. The conversion processor then converts the resulting V2.XML messages to a V3 schema using the methods disclosed herein.

The conversion processor further accepts an XML schema that defines the structure of the desired HL7 V3 message, at a schema accepting step 42. For example, if the required V3 artifact is a clinical document, the XML schema will typically be a CDA, conforming to the CDA specification cited above.

The conversion processor decodes the PID (Patient Identifier) segments of all HL7 V2 messages and maps them to the appropriate sub-tree of the HL7 V3 schema, at a PID mapping step 44. The sub-tree is determined according to a segment conversion table that is stored in mapping database 37 and maintained by the conversion processor, as described hereinbelow. For example, in the CDA schema the PID segment is mapped to the HL7 V3 PatientRole class, which resides in the CDA header.

Some HL7 V2 applications send all patient information (fields in the PID segment) in every message. Other applications, however, send only fields that are updated or changed since the last message. When patient information is modified, an ADT A08 "Update Patient Information" message or an ADT A31 "Update Person Information" message is typically sent. According to the HL7 V2 specification, an A08 message should be used to update patient information for a current episode, while an A31 message should be used to update patient information in a Master Patient Index.

Therefore, in some embodiments of the present invention, the conversion processor retrieves the patient information from the PID segment of the first message of the episode (for example an A01 "Admit Patient" or A04 "Register Patient") at step 44. The conversion processor then checks the fields of the PID segment in each subsequent A08 or A31 message to determine whether there are any changes. In cases where two or more update segments refer to the same data field, the information is taken from the latest segment.

The conversion processor begins to process the V2 messages sequentially at a message picking step 46. For each message in the V2 set, the conversion processor decodes the message type at a message mapping step 48. The message type is found in field 9 of the MSH (Message Header) segment of the V2 message. For example, in the MSH segment "MSH|^~\&|||||19941122100053||ORU^M01|" the message type is "ORU M01". Alternatively, following V2.XML notation, the same message type would be written in the form:

```
<MSH.9>
    <MSG.1>ORU</MSG.1>
    <MSG.2>M01</MSG.2>
</MSH.9>
```

Mapping database 37 comprises a configurable message conversion table, comprising a list of V2 message types and the respective V3 classes to which they should be mapped (sometimes referred to as "target classes"). Each V2 message is mapped to a separate class in the V3 schema, according to the message conversion table. In cases where two or more V2 messages correspond to the same V3 class, they are mapped to different instances (duplicates of classes) within the V3 message or document.

Once each V2 message has been mapped to a corresponding V3 target class, the next step for conversion processor 36 is to map the segments inside the V2 messages to appropriate sub-trees of the V3 schema, at a segment mapping step 50. A sub-tree is an extract of a V3 class, represented by an XML tree. Mapping database 37 comprises a configurable segment conversion table, comprising a list of segment types and the respective V3 schema sub-trees to which they should be mapped. The same segment may appear in different messages in the V2 message set. In this case all such segments are mapped to the same sub-tree structure, but with different parents.

HL7 V2 segments may be repeated several times in a message. Typically, the HL7 V3 schema also permits repeated sub-trees. Otherwise, the conversion processor maps the repeated segments to the same sub-tree structure, but with different parents.

The conversion processor continues the conversion by mapping the HL7 V2 data fields inside the segments to V3 attributes, at a data field mapping step 52. Mapping database 37 comprises a configurable field conversion table defining the V2 data fields and corresponding attributes of the V3 schema that provide the closest semantic match. Each data field is mapped to a V3 attribute according to the field conversion table.

In some cases, the V3 schema may not contain a suitable attribute, or the desired attribute may already contain information from the conversion of a previous data field. In such cases, and whenever a data field cannot be mapped to the main target class: for any reason, the conversion processor creates a "nested RIM class" and maps the data field to that class. A nested class is a new instance ("duplicate") of a RIM class having a COMPONENT relationship with the main target class.

Some V3 schemas do not allow the creation of a nested class. In cases where two or more data fields are mapped to the same attribute, and the V3 schema does not allow nested classes, the conversion processor chooses one field to be mapped according to heuristic criteria. The other data fields may be ignored.

As mentioned above, V2 data fields and V3 attributes are formatted according to specific data types. Typically, V2 and V3 data types are different. Although there are similarities between the data type definitions and names, it is necessary to define the conversion of each V2 data type into the corresponding V3 data type. For this purpose, mapping database 37 comprises a data type conversion table. Additionally, most V3 attributes are designated as CWE ("coded with extension.") i.e., allowing additional codes that are not drawn from the predefined V3 attribute vocabulary. The following table lists several V2 data types and their corresponding V3 counterparts:

| HL7 V2 Data type | HL7 V3 Data type |
|---|---|
| CE | CE |
| CD | CE |
| CX | II |
| XPN | PN |
| XAD | AD |
| SN | REAL/RTO_PQ_PQ/PQ |
| CQ | PQ |
| NM | PQ/REAL |
| TS | TS |
| XCN | II + PN |
| TX | ST |
| DT | TS |
| ST | ST |
| FT | ST |

The conversion processor checks whether all V2 messages have been processed at a checking step 54. If there are messages left for processing, the method returns to message picking step 46 to pick the next V2 message otherwise, the conversion processor outputs the resulting HL7 V3 message and terminates at a termination step 56.

EXAMPLE

Conversion of V2 Messages to V3 CDA

The example described below serves to clarify the conversion method of FIG. 2 detailed hereinabove. The example follows the entire process of converting a set of HL7 V2 messages into a V3 CDA document, according to the CDA specification cited above. An additional example, including samples of HL7 V2, V2.XML and V3 messages describing a real-life medical case is given in Appendix 1 below.

The CDA schema comprises a header and a body. The CDA header identifies and classifies the clinical document and provides information regarding authentication, the encounter, the patient, and the involved providers. The CDA body contains the clinical report, and can either be an unstructured body of information or be comprised of structured markup. The structured markup includes a structured body, which is divided into recursively-nestable sections. A section can contain a single narrative block and any number of entries and external references. The entries represent actual clinical artifacts such as observations, procedures, substance administration (medications), etc.

Consider the following set of HL7 V2 messages: ADT A01 (Admit/Visit), ADT A02 (Transfer), ADT A03 (Discharge), ADT A04 (Register a Patient), ADT A08 (Update), ADT A09 (Patient Departing), ADT A11 (Cancel Admission), ADT A13 (Cancel Discharge), ORM O01 (Pharmacy/Treatment Order), ORU R01 (Observation Reporting), RDE O11 (Pharmacy/Treatment encoded order), OMP O09 (similar to RDE, but without medication-related data and with financial segments), RDS O13 (Pharmacy/Treatment dispensing event), VXU V04 (Vaccination report), DFT (Detail Financial Transactions).

It is required to convert this message set to a V3 CDA schema. The following steps are performed, following the method of FIG. 2:
1. Map the V2 PID segment to the V3 PatientRole class that resides in the CDA header.
2. Map each V2 message in the set to a different Section class in V3 CDA. The two message type codes are mapped to the HL7 V3 Section class title and code. The following configurable table summarizes some of the HL7 V2 message types and their corresponding section titles. (The message code—not shown here—is also included in the V3 class.)

| HL7 V2 message type | V3 section title |
|---|---|
| ADT A01 | Admit/visit |
| ADT A02 | Transfer a patient |
| ADT A03 | Discharge |
| ADT A04 | Register |
| ADT A08 | Update message |
| ADT A09 | Cancel admission or visit |
| ADT A11 | Cancel discharge Or end visit |
| ADT A13 | Post detail financial transactions |
| ORU R01 | Laboratory |
| RDS O13 | Pharmacy/treatment dispense |
| RDE O11 | Pharmacy/treatment encoded order |
| OMP O09 | Pharmacy/treatment order |
| ORM O01 | General order |
| VXU V04 | Vaccination |

3. Map each V2 segment in the set to a sub-tree in the V3 CDA. Note that if the same segment appears in two different messages, the segments will be mapped to an identical sub-tree, but in different sections. The following configurable table lists some of the HL7 V2 segments and their corresponding CDA classes (if more than one class name is given, the first name represents the root class):

| HL7 V2 segment | HL7 V3 CDA class |
|---|---|
| NTE | Observation |
| PR1 | Procedure |
| DG1 | Observation |
| AL1 | Observation |
| PDA | Observation |
| DB1 | Observation |
| ACC | Observation |
| OBR | Observation |
| OBX | Observation |
| RXO | SubstanceAdministration, LabeledDrug, Observation |
| RXR | SubstanceAdministration, PlayingDevice, Procedure |
| RXC | Labeledrug |
| RXD | SubstanceAdministration, LabeledDrug, Observation |
| RXE | SubstanceAdministration, LabeledDrug |
| RXA | SubstanceAdministration, LabeledDrug |

4. Map each V2 data field in the given segments to a V3 attribute in the CDA schema.

Following these four steps, the set of HL7 V2 messages has been converted to an HL7 V3 CDA.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

Appendix 1—Real-Life Messages and Conversion to HL7 CDA

The following sections provide sample HL7 V2 and V3 messages, to demonstrate the method described in FIG. 2 above using a real-life case.

A set of HL7 V2 messages is provided as input, reporting laboratory results of a diabetic patient. Following the disclosed method, the V2 messages were first converted to V2.XML format using a commercial conversion tool by iNTERFACEWARE, Inc., then converted to an HL7 V3 CDA. As the full text of the messages is extremely long, only short excerpts are provided below. These samples are sufficient for visualizing the three formats involved. Note that some identifying information has been replaced with dummy information, for medical privacy reasons.

HL7 V2 Messages

The following is the text of the first two HL7 V2 messages in the set:

Message 1

```
MSH|^~\&|<XXX>||<XXX>|<XXX>|20030926143408||ORU^R01|
    <XXX>|<XXX>|2.4|
PID|||987654^^^&Good Health Clinic||<XXX>||1900|
    F|||||||||<XXX>|
PV1|||<XXX>|
ORC|RE|||||||||<XXX>|<XXX>|<XXX>|<XXX>|||<XXX>|
OBR|||F32539BMET 039Q^1|24321-2^LOINC^BASIC
    METABOLIC PANEL|||20030926101500||||||<XXX>|<XXX>|
    <XXX>|<XXX>||||||||<XXX>|F|BMET^BMET|^^^^R|<XXX>|
OBX|1|NM|2951-2^SODIUM^LOINC|0|144|mM/l|136-146||||F|
OBX|2|NM|2823-3^POTASSIUM^LOINC|0|4.1|mM/l|3.6-5.0||||F|
OBX|3|NM|2075-0^CHLORIDE^LOINC|0|105|mM/l|102-109||||F|
OBX|4|NM|1963-8^CO2^LOINC|0|28|mM/l|25-33||||F|
OBX|5|NM|3094-0^BUN^LOINC|0|7|mg/dl|7-20||||F|
OBX|6|NM|2345-7^GLUCOSE^LOINC|0|134|mg/dl|70-105|H|||F|
OBX|7|NM|2160-0^CREATININE^LOINC|0|0.7|mg/dl|
    0.5-0.9||||F|
OBX|8|NM|17861-6^CALCIUM^LOINC|0|9.5|mg/dl|8.4-9.8||||F|
```

Message 2

```
MSH|^~\&|<XXX>||<XXX>|<XXX>|20030926143408||ORU^R01|
    <XXX>|<XXX>|2.4|
PID|||987654^^^&Good Health Clinic||<XXX>||1900|
    F|||||||||<XXX>|
PV1|||<XXX>|
ORC|RE|||||||||<XXX>|<XXX>|<XXX>|<XXX>|||<XXX>|
OBR|||F32539LIFP 039Q^1|24325-3^LOINC^HEPATIC
    FUNCTION PANEL|||20030926101500||||||<XXX>|<XXX>|
    <XXX>|<XXX>||||||||<XXX>|F|LIFP^LIFP|^^^^R|<XXX>|
OBX|1|NM|2885-2^PROTEIN, TOTAL^LOINC|0|7.3|
    g/dl|6.7-8.6||||F|
OBX|2|NM|1751-7^ALBUMIN^LOINC|0|4.6|g/dl|4.0-5.0||||F|
OBX|3|NM|1975-2^BILIRUBIN, TOTAL^LOINC|0|1.2|
    mg/dl|0.30-1.30||||F|
OBX|4|NM|1968-7^BILIRUBIN, DIRECT^LOINC|0|0.2|
    mg/dl|0.04-0.38||||F|
OBX|5|NM|1920-8^AST^LOINC|0|19|U/l|12-38||||F|
OBX|6|NM|1742-6^ALT^LOINC|0|16|U/l|7-41||||F|
OBX|7|NM|6768-6^ALKALINE PHOSPHATASE^LOINC|0|
    90|U/l|33-96||||F|
```

HL7 V2.XML Message

The following printout is the first part of the V2.XML message, derived from the original set of HL7 V2 messages using a commercial V2 to V2.XML conversion tool, as described hereinabove:

```xml
<HL7v2>
  <Name>some-name</Name>
  <ORU_R01>
    <MSH>
      <MSH.1>|</MSH.1>
      <MSH.2>^~\&</MSH.2>
      <MSH.3>
        <HD.1><XXX></HD.1>
      </MSH.3>
      <MSH.5>
        <HD.1><XXX></HD.1>
      </MSH.5>
      <MSH.6>
        <HD.1><XXX></HD.1>
      </MSH.6>
      <MSH.7>
        <TS.1>20030926143408</TS.1>
      </MSH.7>
      <MSH.9>
        <MSG.1>ORU</MSG.1>
        <MSG.2>R01</MSG.2>
      </MSH.9>
      <MSH.10><XXX></MSH.10>
      <MSH.11>
```

```
    <PT.1><XXX></PT.1>
   </MSH.11>
- <MSH.12>
   <VID.1>2.4</VID.1>
   </MSH.12>
   <MSH.13>0.000000</MSH.13>
  </MSH>
- <ORU_R01.PATIENT_RESULT>
- <ORU_R01.PATIENT>
- <PID>
- <PID.3>
   <CX.1>102275</CX.1>
- <CX.4>
   <HD.2>Good Health Clinic</HD.2>
   </CX.4>
  </PID.3>
- <PID.5>
- <XPN.1>
   <FN.1><XXX></FN.1>
   </XPN.1>
  </PID.5>
- <PID.7>
   <TS.1>1900</TS.1>
  </PID.7>
  <PID.8>F</PID.8>
- <PID.18>
   <CX.1><XXX></CX.1>
  </PID.18>
  <PID.19 />
  </PID>
- <ORU_R01.PATIENT_VISIT>
```

```
- <PV1>
  - <PV1.3>
    <PL.1><XXX></PL.1>
    </PV1.3>
    <PV1.4 />
    </PV1>
    </ORU_R01.PATIENT_VISIT>
    </ORU_R01.PATIENT>
- <ORU_R01.ORDER_OBSERVATION>
- <ORC>
    <ORC.1>RE</ORC.1>
  - <ORC.10>
    <XCN.1><XXX></XCN.1>
    </ORC.10>
  - <ORC.11>
    <XCN.1><XXX></XCN.1>
    </ORC.11>
  - <ORC.12>
    <XCN.1><XXX></XCN.1>
    </ORC.12>
  - <ORC.13>
    <PL.1><XXX></PL.1>
    </ORC.13>
  - <ORC.16>
    <CE.1><XXX></CE.1>
    </ORC.16>
  - <ORC.17>
    <CE.1 />
    </ORC.17>
    </ORC>
- <OBR>
```

```
- <OBR.3>
    <EI.1>F32539BMET 039Q</EI.1>
    <EI.2>1</EI.2>
  </OBR.3>
- <OBR.4>
    <CE.1>24321-2</CE.1>
    <CE.2>LOINC</CE.2>
    <CE.3>BASIC METABOLIC PANEL</CE.3>
  </OBR.4>
- <OBR.7>
    <TS.1>20030926101500</TS.1>
  </OBR.7>
  <OBR.13><XXX></OBR.13>
- <OBR.14>
    <TS.1><XXX></TS.1>
  </OBR.14>
- <OBR.15>
- <SPS.1>
    <CE.1><XXX></CE.1>
  </SPS.1>
  </OBR.15>
- <OBR.16>
    <XCN.1><XXX></XCN.1>
  </OBR.16>
  <OBR.24><XXX></OBR.24>
  <OBR.25>F</OBR.25>
- <OBR.26>
- <PRL.1>
    <CE.1>BMET</CE.1>
  </PRL.1>
  <PRL.2>BMET</PRL.2>
```

```
            </OBR.26>
          - <OBR.27>
            <TQ.1 />
            <TQ.2 />
            <TQ.4 />
            <TQ.5 />
            <TQ.6>R</TQ.6>
            </OBR.27>
          - <OBR.28>
            <XCN.1><XXX></XCN.1>
            </OBR.28>
          - <OBR.29>
          - <EIP.1>
            <EI.1 />
            </EIP.1>
            </OBR.29>
            </OBR>
        - <ORU_R01.OBSERVATION>
        - <OBX>
          <OBX.1>1</OBX.1>
          <OBX.2>NM</OBX.2>
        - <OBX.3>
          <CE.1>2951-2</CE.1>
          <CE.2>SODIUM</CE.2>
          <CE.3>LOINC</CE.3>
          </OBX.3>
          <OBX.4>0</OBX.4>
          <OBX.5>144</OBX.5>
        - <OBX.6>
          <CE.1>mM/l</CE.1>
          </OBX.6>
```

```xml
<OBX.7>136-146</OBX.7>
<OBX.11>F</OBX.11>
<OBX.12>
  <TS.1 />
</OBX.12>
</OBX>
</ORU_R01.OBSERVATION>
<ORU_R01.OBSERVATION>
<OBX>
  <OBX.1>2</OBX.1>
  <OBX.2>NM</OBX.2>
  <OBX.3>
    <CE.1>2823-3</CE.1>
    <CE.2>POTASSIUM</CE.2>
    <CE.3>LOINC</CE.3>
  </OBX.3>
  <OBX.4>0</OBX.4>
  <OBX.5>4.1</OBX.5>
  <OBX.6>
    <CE.1>mM/l</CE.1>
  </OBX.6>
  <OBX.7>3.6-5.0</OBX.7>
  <OBX.11>F</OBX.11>
  <OBX.12>
    <TS.1 />
  </OBX.12>
</OBX>
</ORU_R01.OBSERVATION>
<ORU_R01.OBSERVATION>
<OBX>
  <OBX.1>3</OBX.1>
```

```
<OBX.2>NM</OBX.2>
<OBX.3>
  <CE.1>2075-0</CE.1>
  <CE.2>CHLORIDE</CE.2>
  <CE.3>LOINC</CE.3>
</OBX.3>
<OBX.4>0</OBX.4>
<OBX.5>105</OBX.5>
<OBX.6>
  <CE.1>mM/l</CE.1>
</OBX.6>
<OBX.7>102-109</OBX.7>
<OBX.11>F</OBX.11>
<OBX.12>
  <TS.1 />
</OBX.12>
</OBX>
</ORU_R01.OBSERVATION>
<ORU_R01.OBSERVATION>
<OBX>
  <OBX.1>4</OBX.1>
  <OBX.2>NM</OBX.2>
  <OBX.3>
    <CE.1>1963-8</CE.1>
    <CE.2>CO2</CE.2>
    <CE.3>LOINC</CE.3>
  </OBX.3>
  <OBX.4>0</OBX.4>
  <OBX.5>28</OBX.5>
  <OBX.6>
    <CE.1>mM/l</CE.1>
```

```
        </OBX.6>
        <OBX.7>25-33</OBX.7>
        <OBX.11>F</OBX.11>
-       <OBX.12>
        <TS.1 />
        </OBX.12>
        </OBX>
        </ORU_R01.OBSERVATION>
-     <ORU_R01.OBSERVATION>
-       <OBX>
        <OBX.1>5</OBX.1>
        <OBX.2>NM</OBX.2>
-       <OBX.3>
        <CE.1>3094-0</CE.1>
        <CE.2>BUN</CE.2>
        <CE.3>LOINC</CE.3>
        </OBX.3>
        <OBX.4>0</OBX.4>
        <OBX.5>7</OBX.5>
-       <OBX.6>
        <CE.1>mg/dl</CE.1>
        </OBX.6>
        <OBX.7>7-20</OBX.7>
        <OBX.11>F</OBX.11>
-       <OBX.12>
        <TS.1 />
        </OBX.12>
        </OBX>
        </ORU_R01.OBSERVATION>
-     <ORU_R01.OBSERVATION>
-       <OBX>
```

```
<OBX.1>6</OBX.1>
<OBX.2>NM</OBX.2>
<OBX.3>
<CE.1>2345-7</CE.1>
<CE.2>GLUCOSE</CE.2>
<CE.3>LOINC</CE.3>
</OBX.3>
<OBX.4>0</OBX.4>
<OBX.5>134</OBX.5>
<OBX.6>
<CE.1>mg/dl</CE.1>
</OBX.6>
<OBX.7>70-105</OBX.7>
<OBX.8>H</OBX.8>
<OBX.11>F</OBX.11>
<OBX.12>
<TS.1 />
</OBX.12>
</OBX>
</ORU_R01.OBSERVATION>
<ORU_R01.OBSERVATION>
<OBX>
<OBX.1>7</OBX.1>
<OBX.2>NM</OBX.2>
<OBX.3>
<CE.1>2160-0</CE.1>
<CE.2>CREATININE</CE.2>
<CE.3>LOINC</CE.3>
</OBX.3>
<OBX.4>0</OBX.4>
<OBX.5>0.7</OBX.5>
```

```xml
<OBX.6>
  <CE.1>mg/dl</CE.1>
</OBX.6>
<OBX.7>0.5-0.9</OBX.7>
<OBX.11>F</OBX.11>
<OBX.12>
  <TS.1 />
</OBX.12>
</OBX>
</ORU_R01.OBSERVATION>
<ORU_R01.OBSERVATION>
<OBX>
  <OBX.1>8</OBX.1>
  <OBX.2>NM</OBX.2>
  <OBX.3>
    <CE.1>17861-6</CE.1>
    <CE.2>CALCIUM</CE.2>
    <CE.3>LOINC</CE.3>
  </OBX.3>
  <OBX.4>0</OBX.4>
  <OBX.5>9.5</OBX.5>
  <OBX.6>
    <CE.1>mg/dl</CE.1>
  </OBX.6>
  <OBX.7>8.4-9.8</OBX.7>
  <OBX.11>F</OBX.11>
  <OBX.12>
    <TS.1 />
  </OBX.12>
</OBX>
</ORU_R01.OBSERVATION>
```

</ORU_R01.ORDER_OBSERVATION>
</ORU_R01.PATIENT_RESULT>

HL7 V3 CDA

The following printout is an excerpt from the V3 CDA, derived from the above set of HL7 V2 messages, using the method of FIG. 2:

```xml
<?xml version="1.0" ?>
<ClinicalDocument xmlns="urn:hl7-org:v3"
xmlns:xsi="http://www.w3.org/2001/XMLSchema-instance"
xsi:schemaLocation="urn:hl7-org:v3
CDA.ReleaseTwo.CommitteeBallot02.Dec.2003.xsd">
    <id root="2.16.840.1.113883.3.18" extension="some-
name.1085040298596" />
    <code displayName="Aggregated v2 based CDA" />
    <effectiveTime value="20040520" />
<author>
    <time value="20040520" />
<assignedAuthor>
    <id root="2.16.840.1.113883.3.18" />
<assignedAuthorChoice>
<Device>
    <softwareName>IBM</softwareName>
</Device>
</assignedAuthorChoice>
</assignedAuthor>
</author>
<custodian>
<assignedCustodian>
<representedOrganization>
    <name>IBM </name>
</representedOrganization>
</assignedCustodian>
</custodian>
<recordTarget>
<patientRole>
    <id
extension="<PID.3><CX.1>102275</CX.1><CX.4><HD.2>Good
Health Clinic</HD.2></CX.4></PID.3>" />
    <telecom use="HP" value="XXX" />
    <telecom use="WP" value="XXX" />
<patientPatient>
    <name><XPN.1><FN.1><XXX></FN.1></XPN.1></name>
    <administrativeGenderCode code="F" />
    <birthTime value="1900" />
    <maritalStatusCode code="<XXX>" />
    <religiousAffiliationCode code="<XXX>" />
<languageCommunication>
    <languageCode code="<XXX>" />
</languageCommunication>
</patientPatient>
</patientRole>
</recordTarget>
<component>
<bodyChoice>
<StructuredBody>
<component>
<section>
    <code code="11502-2" codeSystem="2.16.840.1.113883.6.1"
codeSystemName="LOINC" displayName="LABORATORY
REPORT" />
    <title>Laboratory</title>
<text><MSH.1>|</MSH.1><MSH.2>^~\&</MSH.2><MSH.3><HD.1>
<XXX></HD.1></MSH.3><MSH.5><HD.1><XXX></HD.1></MSH.5>
<MSH.6><HD.1><XXX></HD.1></MSH.6><MSH.7>
<TS.1>20030926143408</TS.1></MSH.7><MSH.9><MSG.1>ORU
</MSG.1><MSG.2>R01</MSG.2></MSH.9><MSH.10><XXX>
</MSH.10><MSH.11><PT.1><XXX></PT.1></MSH.11><MSH.12>
<VID.1>2.4</VID.1></MSH.12><MSH.13>0.000000</MSH.13></text>
<entry>
<entryChoice>
<Observation>
    <code code="24321-2" codeSystemName="BASIC METABOLIC
PANEL" displayName="LOINC" />
    <statusCode code="F" />
<effectiveTime>
    <low value="20030926101500" />
</effectiveTime>
<entryRelationship typeCode="COMP">
<entryChoice>
<Observation>
    <code code="<XXX>" displayName="unspecified" />
    <text>Relevant Clinical Information</text>
</Observation>
</entryChoice>
</entryRelationship>
<entryRelationship typeCode="COMP">
<entryChoice>
<Observation>
    <code code="<XXX>" displayName="unspecified" />
    <text>Specimen Source</text>
</Observation>
</entryChoice>
</entryRelationship>
</Observation>
</entryChoice>
</entry>
<entry>
<entryChoice>
<Observation>
    <id extension="1" />
    <code code="2951-2" codeSystem="2.16.840.1.113883.6.1"
codeSystemName="LOINC" displayName="SODIUM" />
    <statusCode code="F" />
<entryRelationship typeCode="COMP">
<entryChoice>
<Observation>
    <code displayName="unspecified" />
    <text>Observation Value</text>
    <value xsi:type="PQ" value="144" unit="mM/l" />
</Observation>
</entryChoice>
</entryRelationship>
<entryRelationship typeCode="COMP">
<entryChoice>
<Observation>
    <code displayName="unspecified" />
    <text>References Range</text>
    <value xsi:type="ST">136-146</value>
</Observation>
</entryChoice>
</entryRelationship>
</Observation>
</entryChoice>
</entry>
<entry>
<entryChoice>
<Observation>
    <id extension="2" />
    <code code="2823-3" codeSystem="2.16.840.1.113883.6.1"
codeSystemName="LOINC" displayName="POTASSIUM" />
    <statusCode code="F" />
<entryRelationship typeCode="COMP">
<entryChoice>
<Observation>
    <code displayName="unspecified" />
    <text>Observation Value</text>
    <value xsi:type="PQ" value="4.1" unit="mM/l" />
</Observation>
</entryChoice>
</entryRelationship>
<entryRelationship typeCode="COMP">
<entryChoice>
<Observation>
    <code displayName="unspecified" />
    <text>References Range</text>
    <value xsi:type="ST">3.6-5.0</value>
</Observation>
</entryChoice>
</entryRelationship>
</Observation>
</entryChoice>
</entry>
<entry>
<entryChoice>
<Observation>
    <id extension="3" />
    <code code="2075-0" codeSystem="2.16.840.1.113883.6.1"
codeSystemName="LOINC" displayName="CHLORIDE" />
```

-continued

```
<statusCode code="F" />
- <entryRelationship typeCode="COMP">
- <entryChoice>
- <Observation>
    <code displayName="unspecified" />
    <text>Observation Value</text>
    <value xsi:type="PQ" value="105" unit="mM/l" />
  </Observation>
  </entryChoice>
  </entryRelationship>
- <entryRelationship typeCode="COMP">
- <entryChoice>
- <Observation>
    <code displayName="unspecified" />
    <text>References Range</text>
    <value xsi:type="ST">102-109</value>
  </Observation>
  </entryChoice>
  </entryRelationship>
  </Observation>
  </entryChoice>
  </entry>
- <entry>
- <entryChoice>
- <Observation>
    <id extension="4" />
    <code code="1963-8" codeSystem="2.16.840.1.113883.6.1" codeSystemName="LOINC" displayName="CO2" />
    <statusCode code="F" />
- <entryRelationship typeCode="COMP">
- <entryChoice>
- <Observation>
    <code displayName="unspecified" />
    <text>Observation Value</text>
    <value xsi:type="PQ" value="28" unit="mM/l" />
  </Observation>
  </entryChoice>
  </entryRelationship>
- <entryRelationship typeCode="COMP">
- <entryChoice>
- <Observation>
    <code displayName="unspecified" />
    <text>References Range</text>
    <value xsi:type="ST">25-33</value>
  </Observation>
  </entryChoice>
  </entryRelationship>
  </Observation>
  </entryChoice>
  </entry>
```

The invention claimed is:

1. A method for converting communications messages, comprising:

accepting a plurality of interrelated input messages to be converted, the messages conforming to a Health Level Seven Version 2 (HL7 V2) specification and comprising segments, wherein a given segment appears in at least two of the messages;

accepting an Extensible Markup Language (XML) schema, which is derived from a Health Level Seven Version 3 (HL7 V3) specification Reference Information Model (RIM);

providing conversion mapping rules, which specify semantic relationships in accordance with the HL7 V3 RIM, for converting first messages conforming to the HL7 V2 specification to second messages conforming to the HL7 V3 specification such that the second messages conform to the semantic relationships; and using the conversion mapping rules, automatically converting the plurality of the interrelated input messages to at least one of a single V3 message and a single V3 document, comprising data elements that conform to the semantic relationships, by mapping segments of the input messages to XML sub-trees of a class in the XML scheme, wherein the given segment in the at least two of the messages is mapped to different parts of an identical sub-tree.

2. The method according to claim 1, wherein converting the input messages comprises mapping a Patient Identification (PID) segment in at least one of the input messages to an XML sub-tree in the XML schema in accordance with the conversion mapping rules.

3. The method according to claim 1, wherein converting the input messages comprises mapping at least one of the input messages to a class in the XML schema in accordance with the conversion mapping rules.

4. The method according to claim 3, wherein the at least one of the input messages comprises a header that defines a message type, and wherein mapping the at least one of the input messages comprises decoding the message type and defining the class in accordance with the message type.

5. The method according to claim 3, wherein mapping the at least one of the input messages comprises mapping segments of the at least one of the input messages to XML sub-trees of the class, in accordance with the conversion mapping rules.

6. The method according to claim 5, wherein the XML sub-trees comprise attributes, and wherein mapping the segments comprises mapping data fields in the segments of the at least one of the input messages to the attributes, in accordance with the conversion mapping rules.

7. The method according to claim 6, wherein the attributes are formatted according to a data type, and wherein mapping the data fields to the attributes comprises reformatting the data fields according to the data type.

8. The method according to claim 6, wherein mapping the data fields comprises creating a nested class in the XML sub-trees and mapping the data fields to the attributes of the nested class.

9. The method according to claim 1, wherein converting the input messages comprises converting the input messages to an HL7 V2.XML format, and mapping the messages from the HL7 V2.XML format to the single V3 message or document.

* * * * *